US006232512B1

(12) United States Patent
Haas et al.

(10) Patent No.: US 6,232,512 B1
(45) Date of Patent: May 15, 2001

(54) METHOD FOR REDUCING THE CONTENT OF ACETALS OR KETALS IN ALCOHOL-CONTAINING REACTION MIXTURES

(75) Inventors: Thomas Haas, Frankfurt; Bernd Jäger, Darmstadt; Jörg Sauer, Rodenbach; Rudolf Vanheertum, Kahl, all of (DE)

(73) Assignee: Degussa-Huls AG, Frankfurt am Main (DE)

( * ) Notice: Subject to any disclaimer, the term of this patent is extended or adjusted under 35 U.S.C. 154(b) by 0 days.

(21) Appl. No.: 09/386,415

(22) Filed: Aug. 31, 1999

(30) Foreign Application Priority Data

Sep. 4, 1998 (DE) .............................................. 198 40 277

(51) Int. Cl.⁷ ............................ C07C 29/88; C07C 29/90
(52) U.S. Cl. .................. 568/914; 568/852; 568/862; 568/863; 568/868; 568/882; 568/884; 568/885; 568/913
(58) Field of Search ..................... 568/852, 862, 568/863, 868, 882, 884, 885, 913, 914

(56) References Cited

U.S. PATENT DOCUMENTS

| 2,569,671 | 10/1951 | Hughes | 260/643 |
|---|---|---|---|
| 3,819,728 | 6/1974 | Kwantes | 260/643 B |
| 4,044,059 | 8/1977 | Copelin | 260/635 |
| 4,401,834 | 8/1983 | King | 568/881 |

FOREIGN PATENT DOCUMENTS

| 42 20 939 A1 | 1/1994 | (DE) . |
|---|---|---|
| 0 572 812 A1 | 12/1993 | (EP) . |
| WO 97/01523 | 1/1997 | (WO) . |
| WO 97/36846 | 10/1997 | (WO) . |

OTHER PUBLICATIONS

Elliott et al., "Chemical Processing in High–Pressure Aqueous Environments. 4. Continuous–Flow Reactor Process Development Experiments for Organics Destruction", Ind. Eng. Res. (1994) vol. 33, pp. 566–574.

Derwent WPI, "2–Aryl–Ethanol Compounds From . . . Useful as Aroma or Fragrance", Abstract DE 4220939 (1994).

Primary Examiner—Peter O'Sullivan
(74) Attorney, Agent, or Firm—Pillsbury Winthrop LLP

(57) ABSTRACT

Reduction in the content of acetals or ketone acetals in a reaction mixture containing at least 10 moles alcohol per mole acetal or ketone acetal can be achieved hydrogenolytically when the reaction mixture is hydrogenated at 80° to 250° C. at a hydrogen partial pressure of 0.5 to 30 MPa in the presence of activated carbon charged with noble metal as catalyst.

8 Claims, No Drawings

METHOD FOR REDUCING THE CONTENT OF ACETALS OR KETALS IN ALCOHOL-CONTAINING REACTION MIXTURES

CROSS-REFERENCE TO RELATED APPLICATION

This application is based on German Application DE 198 40 277.5, filed Sep. 4, 1998, which disclosure is incorporated herein by reference.

FIELD OF THE INVENTION

The invention relates to a method for reducing the content of acetals or ketone acetals (ketals) in an aqueous reaction mixture containing at least 10 moles of a mono- or polyvalent alcohol per mole of the acetal or ketal by heterogeneous, catalytic hydrogenation.

BACKGROUND OF THE INVENTION

During the hydrogenation of aldehydes and ketones to alcohols the formation of acetals and ketals readily occurs if the hydrogenation is carried out below pH 7 or in the presence of solid catalysts comprising acidic centers. The acetals and ketals cannot be satisfactorily converted into the alcohols forming the basis and formed from the carbonyl compound by mild hydrogenation. Stable cyclic acetals and ketals, namely, 2-substituted 1,3-dioxolane- and 1,3-dioxan derivatives are produced in particular during the hydrogenation of α- and β-hydroxycarbonyl compounds to 1,2- and 1.3-diols. In order to hydrogenate such acetals and ketals, rather high temperatures and/or special catalysts are required. One problem in reducing the content of acetals and ketals in aqueous, alcoholic reaction mixtures of differing provenance also resides additionally in the fact that there is a danger that the alcohol itself will be decomposed under the rather severe hydrogenation conditions required.

3-Hydroxypropionaldehyde is reduced to 1,3-propane diol in the method of EP-A 0 572 812 in which a first hydrogenation stage for the purpose of reducing the content of residual carbonyl is followed by a second hydrogenation stage at a pH of 2.5 to 6.5 at an elevated temperature. The same hydrogenation catalyst was used in both temperature stages, preferably a Pt/TiO$_2$-carrier catalyst and Ni/Al$_2$O$_3$/SiO$_2$-carrier catalyst. It was determined that only an unsatisfactory conversion can be achieved in the second stage with a noble metal catalyst on an oxide carrier, with a neutral or weakly acid pH range; in addition, the catalytic activity drops after a few hours of operation to a level which is lower than at the beginning.

According to WO 97/01523 cyclic diethers can be hydrogenolytically split with a 1,3-dioxo group in an aqueous phase in the presence of a metallic catalyst such as Ru on activated carbon at 100° to 200° C. at a pH of 1 to 6. According to the examples the degree of conversion is not quantitative. In particular, this document furnishes no suggestion for degrading small amounts of acetal or ketal in addition to large amounts of an alcohol without also decomposing the alcohol at the same time by hydrogenolysis. In addition, a very high ratio of catalyst to substrate is required in order to bring about the conversion. In a similar manner the hydrogenolytic splitting of 1,3-dioxan derivatives is incomplete if Raney nickel is used as catalyst, according to U.S. Pat. No. 4,044,059.

In order to reduce the carbonyl content of lauryl alcohol containing 0.1% by weight lauryl aldehyde by catalytic hydrogenation, nickel catalyst on kieselguhr diatomaceous earth is recommended as the catalyst according to the brochure "Carbonyl Removal from Oxoalcohols" (Engelhard Corp.) even though this company also supplies carrier-bound noble-metal catalysts. Nickel catalysts tend to leach metal at a pH below 7, which has a disadvantageous effect on the workup.

Ind. Eng. Chem. Res. 33 (1994), 566–574 teaches the degradation of organic components such as sugar and glycols in aqueous media hydrogenolytically in the presence of Ni catalysts or ruthenium on various oxide carriers. When using such catalysts to reduce the acetal content or ketal content in an aqueous medium containing an excess of an alcohol with respect to the amount of the acetal or ketal a partial degradation of the alcohol must be expected in the process described.

SUMMARY OF THE INVENTION

The invention has the object of making available a method in which a low acetal content or ketal content in an aqueous reaction mixture, which has a high content of alcohols, which is acid or neutral at room temperature, can be further reduced essentially without degradation of the alcohols.

A method has been found for reducing the content of acetals (except formals) or ketals in an aqueous reaction mixture containing at least 10 moles of a monovalent or polyvalent alcohol per mole of the acetal or ketal by heterogeneous, catalytic hydrogenation of the reaction mixture with hydrogen, at a temperature of 80° to 250° C. and a hydrogen partial pressure of 0.5 to 30 MPa, particularly 1 to 15 MPa, which is characterized in that activated carbon charged with noble metal is used as catalyst.

Preferred embodiments include the hydrogenation of reaction mixtures containing a cyclic acetal or ketal with a 1,3-dioxo structure, use of Pd and/or Ru on activated carbon as the catalyst, carrying out the method using a trickle-bed reactor and carrying out the method using a solution with a pH of between above 6.5 and 7.

It is surprisingly possible to increase the amount of hydrogenation of the acetal or ketal contained in the reaction mixture at the same temperature and at the same pH without the alcohol present being decomposed to any appreciable extent at the same time, if an activated carbon charged with noble metal such as an activated carbon charged with one or more noble metals from the group Ru, Rh, Pd and Pt is used instead of an oxide catalyst charged with the noble metal. As follows from the examples, when Ru on TiO$_2$ is used, a quantitative reaction of the acetal does take place but, at the same time, decomposition of the alcohol occurs to an intolerable extent. Other catalysts known for the hydrogenation of acetals and the carbonyl compound on which they are based, for example, Ni on SiO$_2$/Al$_2$O$_3$ carrier, do not attack the alcohol; however, their hydrogenation activity is insufficient if only a small amount of acetal is contained in the reaction mixture in addition to a large amount of alcohol. Especially preferred catalysts to be used in accordance with the invention are Ru and/or Pd on activated carbon, wherein "activated carbon" includes all types of carbon suitable for catalytic purposes.

The hydrogenation customarily takes place at 80° to 250° C., preferably at 100° to 180°C. If the alcohol content drops during the hydrogenation, this reduction of alcohol content can generally be reduced or entirely avoided without any appreciable reduction of the hydrogenation conversion by reducing the reaction temperature.

The hydrogenation usually takes place at a pH range from 1 to below 7, measured at the reaction temperature. The method of the invention has the advantage that the reaction mixture to be used can have a pH of between above 6.5 and 7 at room temperature since this simplifies the workup.

The reaction mixture supplied to the hydrogenation reaction contains a high molar excess of alcohol in comparison to the acetal or ketal, namely, at least 10 moles and preferably at least 50 moles alcohol per mole acetal or ketal. The alcohol can be any alcohol since the source of the reaction mixture can be as desired; however, it is preferable that the alcohol is bound in the acetal or ketal and/or produced during the hydrogenation. The method is suited in particular for removing acetals, except for formals, or ketals of α- or β-hydroxycarbonyl compounds out of reaction mixtures. The acetals and ketals are, in particular, cyclic compounds with a 1,3-dioxo structure, especially 1,3-dioxan compounds and 1,3-dioxolane compounds. During the hydrogenolytic splitting of the ring a 1,3-diol or 1,2-diol and the alcohol formed from the aldehyde or ketone are produced. Cyclic acetals with a 1,3-dioxo structure which are not substituted in the 2-position (this concerns formals) can be split only partially hydrogenolytically under customary conditions.

The method can be carried out continuously or batchwise, e.g., in a suspension method or a fixed-bed method. It is especially preferable to carry out the hydrogenation using a trickle-bed reactor. The fixed-bed catalysts to be used therewith are preferably pellets with a diameter of 0.5 to 5 mm, especially 1 to 3 mm, and with a length of 1 to 10 mm. The noble-metal content of such catalysts is in the customary range, usually 0.5 to 5% by weight.

The method of the invention is distinguished in that even a small content of acetals or ketals can be further reduced hydrogenolytically in the reaction mixture without any appreciable attack on the formed alcohol or alcohols present. This surprising effect is illustrated using the following examples and reference examples.

DETAILED DESCRIPTION OF THE PREFERRED EMBODIMENTS

EXAMPLES

A trickle-bed system with 15 ml reactor volume was used for the continuous hydrogenation in a trickle bed. The system included a liquid receiver, a pre-heater, a fixed-bed reactor and a liquid separator. The reactor was heated to the desired reaction temperature $T_R$ via a heating system using heat transfer oil. The hydrogen flow rate was 13 Nl/h. Pressure and hydrogen flow were regulated electronically. The aqueous educt solution was charged in front of the pre-heater to the hydrogen flow with a pump and the mixture added at the reactor head (trickle-bed method). After having passed through the reactor, the reaction product was removed at regular intervals ($t_R$) from the liquid separator. The product was analyzed using gas chromatography to determine the amount of 2-(2'-hydroxyethyl)-1,3-dioxan (HED) and 1,3-propane diol (PDO).

Catalysts used:

Ru/AK (a): Activated carbon extrudate with 2% Ru; d = 2.3 mm
(b): Activated carbon extrudate with 3% Ru; d = 2 mm
Pd/AK: Activated carbon extrudate with 2% Pd; d = 1.5 mm
Ru/SiO$_2$: Granulate with 2% Ru; d = 1–2 mm
Ru/Al$_2$O$_3$: Extrudate with 2% Ru; d = 3 mm -continued Ru/TiO$_2$: Extrudate with 2% Ru; d = 1 mm
Ni/SiO$_2$/Al$_2$O$_3$: Extrudate with 30% Ni; d = 1.6 mm ("AK" represents activated carbon)

All the catalysts except the commercial Ni catalyst were produced according to the incipient wetness method using RuCl$_3$ or PdCl$_2$ (Preparation of Catalyst, Delmon, B. et al., Elsevier, Amsterdam, 1976, page 13).

The aqueous solutions used in Examples 1 to 10 contained 1,3-propane diol (PDO) and 2-(2'-hydroxyethyl)-1,3-dioxan (HED), namely, 19.92% by weight PDO and 0.09% by weight HED in Example 1 and 18.61% by weight PDO and 0.09% by weight HED in Examples 2 to 10. In Example 11, an aqueous solution of 0.1% by weight 2-(2'-hydroxyethyl)-5,5-dimethyl-1,3-dioxan (HEDD) and 20% by weight neopentylglycol (NPG) were used. In Example 12, an aqueous solution of 0.1% by weight 2-(2'-benzoyloxyethyl)-5,5-dimethyl-1,3-dioxan (BEDD) and 20% by weight neopentylglycol was used.

The reaction temperature ($T_R$), the LHSV value (liquid hourly space velocity), the pH of the educt solution and analysis data are shown Tables 1 and 2. The data concern products that were obtained after 16 to 28 hours of continuous operation.

TABLE 1

Examples 1 to 10 (LHSV: 2 h$^{-1}$)

| Example No. | Catalyst | $T_R$(° C.) | pH | Conversion HED % | Concentration of PDO after the reaction (%) |
|---|---|---|---|---|---|
| 1 | Ru/AK(a) | 130 | 4 | 92 | 20.03 |
| 2 | Ru/AK(a) | 130 | 7 | 42 | 18.58 |
| 3 | Ru/SiO$_2$ | 130 | 7 | 7 | 17.03 |
| 4 | Ru/TiO$_2$ | 130 | 7 | 19 | 16.60 |
| 5 | Ru/Al$_2$O$_3$ | 130 | 7 | 0 | 18.22 |
| 6 | Ru/AK(b) | 130 | 7 | 30 | 18.44 |
| 7 | Pd/AK | 130 | 7 | 65 | 18.71 |
| 8 | Ni/SiO$_2$/Al$_2$O$_3$ | 130 | 7 | 19 | 18.70 |
| 9 | Ru/AK(a) | 150 | 7 | 73 | 17.03 |
| 10 | Pd/AK | 150 | 7 | 80 | 18.66 |

It follows from the Examples that, using Ru/AK and Pd/AK at 130° C. and 150° C., results in average to good reduction of the acetal HED; however, at 150° C. there is a tendency in the case of Ru/AK for the alcohol content also to be reduced. In the case of Ru/AK a weakly acidic pH favors the reduction of HED. The oxide carrier catalysts result in a low conversion of HED and (except for Example 8) in a strong degradation of the alcohol.

TABLE 2

Examples 11 to 13 (LHSV: 3 h$^{-1}$)

| Example No. | Reaction mixture | Catalyst | $T_R$ (° C.) | pH | Alcohol*) Before reaction | Alcohol*) After reaction | Dioxan derivative*) Before reaction | Dioxan derivative*) After reaction |
|---|---|---|---|---|---|---|---|---|
| 11/1 | HEDD/NPG | Ru/AK(b) | 150 | 7 | 99.13 | 98.28 | 0.43 | 0.11 |
| 11/2 | " | | 130 | 7 | 99.16 | 99.08 | 0.30 | 0.09 |
| 11/3 | " | | 150 | 5 | 99.13 | 98.61 | 0.43 | 0.08 |
| 11/4 | " | Pd/AK | 150 | 7 | 99.13 | 99.24 | 0.43 | 0.08 |
| 11/5**) | " | Pd/TiO$_2$ | 150 | 7 | 99.13 | 99.13 | 0.43 | 0.37 |
| 11/6**) | " | Ru/TiO$_2$ | 150 | 7 | 99.13 | 40.02 | 0.43 | 0 |
| 11/7**) | " | Ru/SiO$_2$ | 150 | 7 | 99.13 | 55.52 | 0.43 | 0 |
| 11/8**) | " | Ni/SiO$_2$/Al$_2$O$_3$ | 150 | 5 | 99.13 | 99.32 | 0.43 | 0.27 |
| 12 | BEDD/NPG | Ru/AK | 150 | 7 | 98.77 | 98.53 | 0.80 | 0 |
| 13***) | 1,3-dioxan (0.1%) and PDO (20%) | Ru/AK | 150 | 7 | 99.31 | 97.64 | 0.55 | 0.46 |

*)Surface %
**)Catalysts not in accordance with the invention
***)Reaction mixture not in accordance with the invention According to the invention a good degradation of the dioxan derivative is achieved with no or only a very slight decomposition of the alcohol. Catalysts not in accordance with the invention result in an insufficient degradation of the dioxan derivative or in a good degradation with a significant decomposition of the alcohol at the same time. Example 13 shows that a slight content of a cyclic formal can be insufficiently reduced.

What is claimed is:

1. A method for reducing the content of acetals, except formals, or ketals in an aqueous reaction mixture containing at least 10 moles of a mono- or polyvalent alcohol per mole of the acetal or ketal by heterogeneous, catalytic hydrogenation of the reaction mixture with hydrogen at a temperature of 80° to 250° C. and a hydrogen partial pressure of 0.5 to 30 MPa, comprising using activated carbon charged with noble metal as catalyst.

2. The method according to claim 1, wherein the reaction mixture contains as the acetal or the ketal, an acetal derivative or ketal derivative of an α- or β-hydroxycarbonyl compound and, as the alcohol, a 1,2-diol or 1,3-diol which can be obtained by hydrogenation of the hydroxycarbonyl compound.

3. The method according to claim 1, wherein the derivative comprises a 1,3-dioxolane derivative or 1,3-dioxan derivative.

4. The method according to claim 1, wherein the catalyst comprises activated carbon and at least one member selected from the group consisting of Pd and Ru deposited thereon.

5. The method according to claim 1, comprising:

carrying out the catalytic hydrogenation using a catalytic fixed bed, wherein the reaction mixture containing the acetal or ketal and the alcohol in dissolved form trickles over the fixed bed.

6. The method according to claim 1, comprising carrying out the catalytic hydrogenation wherein the reaction mixture has a pH in a range of between above 6.5 and 7, measured at 20° C.

7. The method according to claim 1, wherein the reaction mixture that is hydrogenated contains, per mole acetal or ketal, at least 50 moles of the alcohol bound in the acetal or ketal.

8. The method according to claim 1, wherein the reaction mixture that is hydrogenated contains, per mole acetal or ketal, at least 50 moles of the alcohol, wherein the alcohol is produced during the hydrogenation.

* * * * *